United States Patent [19]

Ulrich et al.

[11] Patent Number: 5,325,850
[45] Date of Patent: Jul. 5, 1994

[54] SUCTION CATHETER ASSEMBLIES

[75] Inventors: Karl Ulrich, Belmont; Tom Devlin, Cambridge, both of Mass.

[73] Assignee: Smith Industries Medical Systems, Inc., Keene, N.H.

[21] Appl. No.: 953,932

[22] Filed: Sep. 30, 1992

[51] Int. Cl.⁵ .................................. A61M 16/00
[52] U.S. Cl. .................... 128/200.26; 128/207.14; 128/207.16
[58] Field of Search .............. 128/200.26, 207.14, 128/207.15, 207.16; 604/35, 36, 163, 171

[56] References Cited

U.S. PATENT DOCUMENTS

| | | | |
|---|---|---|---|
| 3,991,762 | 11/1976 | Radford | 604/119 |
| 4,178,936 | 12/1979 | Newcomb | 604/43 |
| 4,342,315 | 8/1992 | Jackson | 604/35 |
| 4,351,328 | 9/1982 | Bodai | 128/202.16 |
| 4,416,273 | 11/1983 | Grimes | 128/207.16 |
| 4,515,592 | 5/1985 | Frankhouser | 604/163 |
| 4,834,710 | 5/1989 | Fleck | 604/171 |
| 4,874,364 | 10/1989 | Morris et al. | 604/35 |
| 4,875,718 | 10/1989 | Marken | 128/912 |
| 5,088,486 | 2/1992 | Jinotti | 128/207.14 |
| 5,125,893 | 6/1992 | Dryden | 604/54 |
| 5,139,018 | 8/1992 | Brodsky et al. | 128/207.14 |
| 5,140,983 | 8/1992 | Jinotti | 128/207.14 |

*Primary Examiner*—Edgar S. Burr
*Assistant Examiner*—Aaron J. Lewis
*Attorney, Agent, or Firm*—Pollock, Vande Sande & Priddy

[57] ABSTRACT

A closed system suction catheter assembly has an aspirating catheter with a radially-projecting portion or flanges at its distal end. The catheter extends through a patient connecting member which is internally shaped to cooperate with the projection on the catheter so that, when the catheter is pulled proximally to its full extent, the projections seal within the patient connecting member.

10 Claims, 2 Drawing Sheets 5,325,850

SUCTION CATHETER ASSEMBLIES

BACKGROUND OF THE INVENTION

This invention relates to suction catheter assemblies.

The invention is more particularly concerned with closed system suction catheter assemblies of the kind having an aspirating catheter enclosed within a protective, flexible sleeve and which can be advanced through a coupling at one end of the assembly. The coupling has one port connected to a tracheal tube and two further side ports by which ventilation of the patient can take place. In use, the machine, proximal end of the catheter is connected to a suction source via a valve. Secretions that build up on the inside of the tracheal tube, the trachea and bronchi can be periodically removed by opening the valve and advancing the catheter through the coupling and down the tracheal tube. The coupling enables ventilation of the patient to continue while suctioning takes place.

One problem with this kind of assembly is that air from the ventilation system can be forced back into the sleeve causing it to inflate. This is undesirable and can make subsequent use of the assembly more difficult.

Although a sliding seal can be provided in the coupling with the outside of the catheter, this does not provide a total air seal; attempts to improve the seal by making it a tighter fit tend to cause an indentation in the catheter especially when it is stored for prolonged periods. One way of preventing the accumulation of air in the sleeve is to provide a small vent that allows air to escape to atmosphere. This, however, is not desirable because it can allow the escape of contaminated material from the assembly onto the user.

Examples of catheter assemblies having an aspirating catheter which is contained within a sleeve and which can be pushed through a sliding seal on a coupling are described in several patents, such as U.S. Pat. No. 3,991,752 to Radford; U.S. Pat. No. 4,569,344 to Palmer; U.S. Pat. No. 4,638,539 to Palmer; U.S. Pat. No. 4,696,296 to Palmer; U.S. Pat. No. 4,825,859 to Lambert; U.S. Pat. No. 4,834,726 to Lambert; U.S. Pat. No. 4,836,199 to Palmer; U.S. Pat. No. 4,838,255 to Lambert; U.S. Pat. No. 4,872,579 to Palmer; U.S. Pat. No. 4,938,741 to Lambert; U.S. Pat. No. 4,967,743 to Lambert; U.S. Pat. No. 4,981,466 to Lambert; U.S. Pat. No. 5,025,806 to Palmer; U.S. Pat. No. 5,029,580 to Radford; U.S. Pat. No. 5,060,646 to Page; U.S. Pat. No. 5,065,754 to Jensen; U.S. Pat. No. 5,073,164 to Hollister; and GB 2207736 to Hollister. Suction catheter assemblies of this kind are also available from Smiths Industries Medical Systems Inc under the trade mark STERI-CATH and from Ballard Medical Products Inc under the trade mark TRACHCARE.

SUMMARY OF THE INVENTION

It is an object of the present invention to provide a suction catheter assembly in which there is a reduced risk of inflation of the sleeve and in which the user is protected from contact with contaminated material.

According to one aspect of the present invention there is provided a suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a first sliding seal which seals with the outside of the aspirating catheter; a protective sleeve surrounding at least the majority of the length of the catheter where it extends between the vacuum connecting member and the patient connecting member, the protective sleeve being adapted to permit the distal end of the catheter to be extended from the protective sleeve into the patient and to be withdrawn from the patient; and the aspirating catheter having a radially enlarged portion close to its distal end which forms a second fluid seal with the inside of the patient connecting member when the aspirating catheter is pulled proximally to its full extent into the protective sleeve.

The patient connecting member preferably has a tubular portion with a distal region and a proximal region, the distal region having an internal diameter that is the same as the external diameter of the enlarged portion of the catheter and the proximal region having an internal diameter slightly greater than the external diameter of the aspirating catheter proximally of the enlarged portion such that the enlarged portion of the catheter forms a fluid seal with the distal region of the tubular portion of the patient connecting member. The tubular portion of the patient connecting member preferably has a shoulder between the proximal and distal regions, the aspirating catheter having a shoulder between the enlarged portion of the catheter and that part of the catheter proximally of the enlarged portion, the shoulders of the patient connecting member and the aspirating catheter being of cooperating shape and engaging one another when the catheter is pulled proximally to its full extent into the protective sleeve. The radially enlarged portion may be of constant external diameter and extend along the catheter for a distance exceeding the external diameter. Alternatively, the aspirating catheter may have a plurality of radially enlarged portions in the form of a plurality of projecting flanges spaced from one another along the distal end of the catheter. The radially enlarged portion may be of frusto-conical shape, the patient connecting member having a frusto-conical region in which the enlarged portion of the catheter seals when the catheter is pulled proximally to its full extent. The sliding seal may allow a limited gas flow into the protective sleeve when the aspirating catheter is in a position in which the radially enlarged portion is located in a distal position where it does not form a fluid seal with the patient connecting member. The sliding seal may be provided by a member made of a sponge material.

According to another aspect of the present invention there is provided a suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a sliding seal with the outside of the aspirating catheter, the sliding seal allowing a limited fluid flow through it; a protective sleeve surrounding at least the majority of the length of the catheter where it extends between the vacuum connecting member and the patient connecting member, the protective sleeve being adapted to permit the catheter to be extended from the protective sleeve into the patient and to be withdrawn from the patient; and wherein the distal end of the aspirating catheter and the patient connecting member are configured to prevent fluid flow between the patient connecting member and the catheter when the aspirating catheter is withdrawn from the patient into a proximal position.

According to a further aspect of the present invention there is provided a method of suctioning a patient comprising the steps of: providing a suction catheter assembly comprising an aspirating catheter having a proximal end and a distal end, a vacuum connecting member located in the vicinity of the proximal end of the catheter, a patient connecting member mounted to surround the aspirating catheter in the vicinity of the distal end of the aspirating catheter, the patient connecting member having a sliding seal with the outside of the aspirating catheter, and a protective sleeve surrounding at least the majority of the length of the catheter where it extends between the vacuum connecting member and the patient connecting member; connecting the patient connecting member to a tracheal tube; connecting the vacuum connecting member to a vacuum source; advancing the aspirating catheter distally by manipulation through the protective sleeve into the tracheal tube to effect suctioning; and subsequently pulling the aspirating catheter proximally to its full extent such that only in this position the catheter forms a seal with the patient connecting member additional to the sliding seal.

DESCRIPTION OF THE PREFERRED EMBODIMENTS

Figure 1:
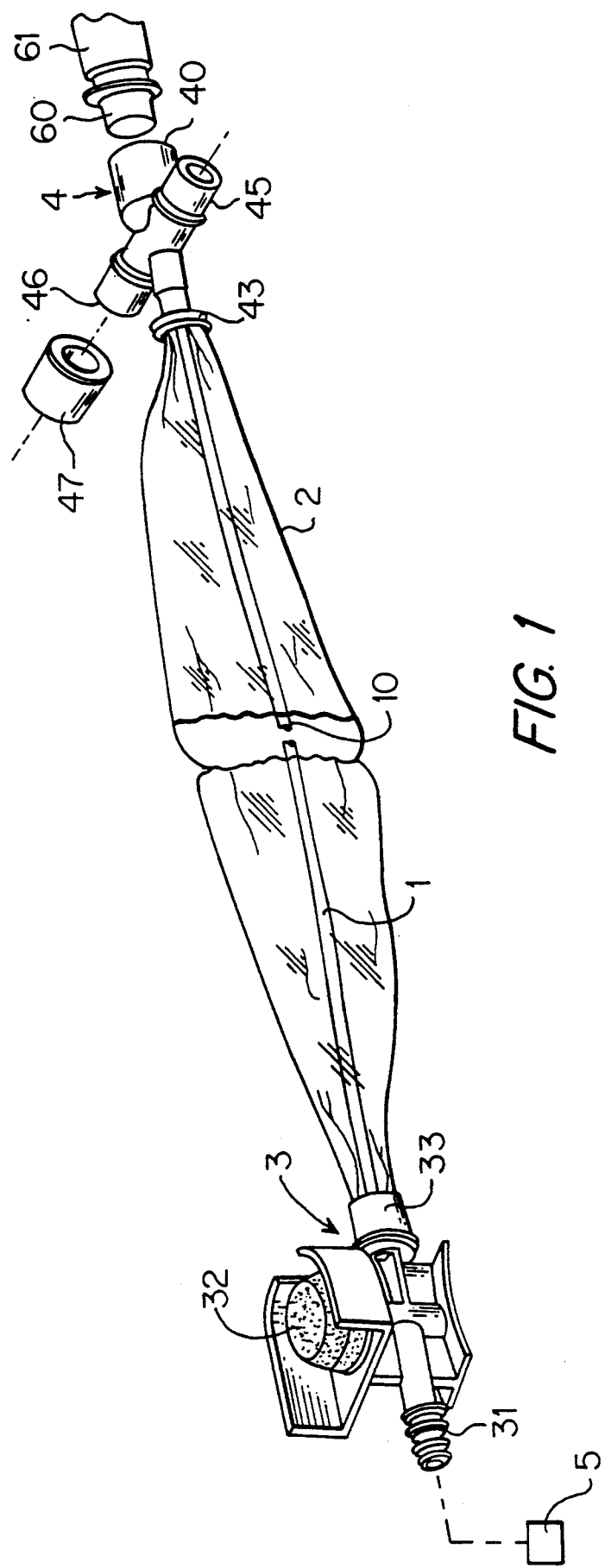
FIG. 1 is a perspective view of the assembly.
Figure 2:
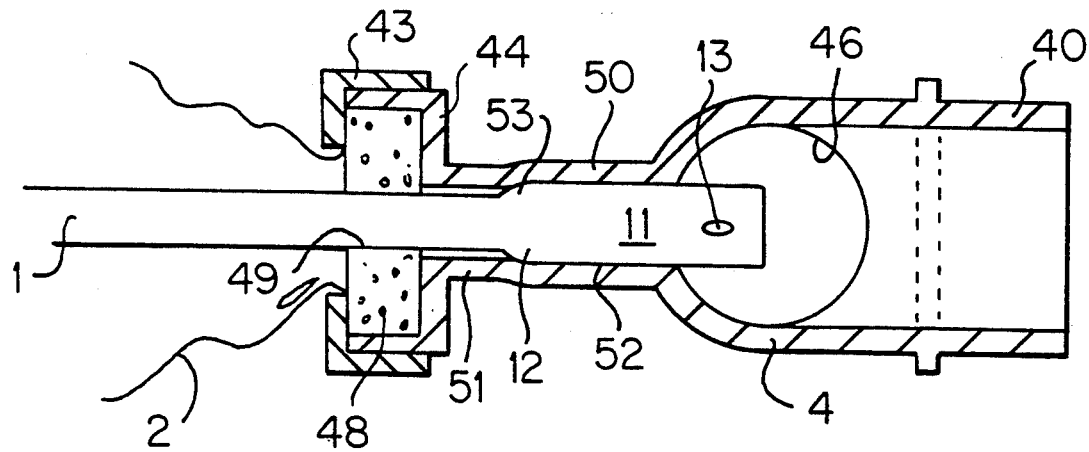
FIG. 2 is an enlarged sectional side elevation of the patient connecting member showing a first embodiment of the present invention.

With reference to FIGS. 1 and 2, the suction catheter assembly comprises an aspirating catheter 1 that extends within a flexible, protective sleeve 2 between a vacuum connecting member 3 and a patient connecting member 4.

The aspirating catheter 1 has a length of about 55 cm and a circular section with an outside diameter of about 4-5 mm along a major part of its length. In the illustrated example, the catheter 1 has a single lumen 10 although catheters with multiple lumens for use in irrigation and/or oxygen supply could be used. At its machine or proximal end, the catheter 1 is secured to the vacuum connecting member 3.

The vacuum connecting member 3 is moulded from a rigid plastics material and has a bore (not shown) extending along it into one end of which the catheter 1 is bonded. The opposite end of the bore extends through a spigot 31 which, in use, is connected to tubing (not shown) which extends to a vacuum or suction source 5. The vacuum connecting member 3 includes a conventional manually-operated valve 32 which normally prevents flow through the connecting member 3 and catheter 1 but which can be pressed down by the user to open the valve and connect the lumen 10 of the catheter to the suction source 5.

The proximal end of the sleeve 2 is secured to the vacuum connecting member 3 beneath a threaded collar 33 secured to the distal end of the vacuum connecting member. The distal end of the sleeve 2 is similarly secured to the patient connecting member 4 by means of a threaded collar 43 which is screwed onto a radially-enlarged, threaded, proximal extension 44 of the patient connecting member.

The patient connecting member 4 is of generally cruciform shape. At its distal, or patient end, the connecting member 4 has a female luer coupling 40 which is aligned with the axis of the member and with the proximal extension 44. The coupling 40 is adapted to be connected to a cooperating coupling 60 on the end of a tracheal tube 61. Two side ports 45 and 46 extend at right angles to the axis of the connecting member, directly opposite one another, about midway along the length of the connecting member. These two side ports 45 and 46 communicate directly with the interior of the coupling 40 and are used in the conventional manner to connect with ventilation apparatus. One port may be used for inhalation gas and the other port used for exhalation gas. Alternatively, one of the ports 46 may be closed by a cap 47 and inhalation and exhalation both be effected through the other port 45.

The aspirating catheter 1 is enlarged externally and internally at its distal end to form an enlarged portion 11 with a constant diameter of about 7 mm and a length of about 22 mm. The length of the enlarged portion 11 thereby exceeds its external diameter. A short, convex tapered region or shoulder 12, about 2 mm in length, extends between the enlarged region 11 and the main body of the catheter 1. The catheter 1 may have an optional side aperture 13 located about 2 mm from the distal end.

Mounted in the proximal end of the patient connecting member 4 is a sponge disc 48 which has a central aperture 49 which embraces the aspirating catheter 1. The disc 48 is located in the proximal extension 44 and is clamped in position by the collar 43.

Between the extension 44 and the side ports 45 and 46, the patient connecting member 4 has an intermediate tubular portion 50. At its proximal end 51, the internal diameter of the portion 50 is slightly greater than the external diameter of the aspirating catheter 1 along the major part of its length, so as to allow free sliding movement of the catheter through the intermediate portion. At its distal end 52, the internal diameter of the intermediate portion 50 is the same as the external diameter of the enlarged region 11 of the catheter, so that the distal end of the catheter is close sliding fit within the distal end of the intermediate portion. The proximal and distal ends 51 and 52 of the intermediate portion 50 are linked by an internal shoulder 53 which is the same shape as the shoulder 12 on the catheter 1. In this way, the interior of the distal end of the intermediate portion 50 has the same profile as the exterior of the enlarged region 11 of the catheter.

In the position illustrated in FIG. 2, the catheter 1 is pulled proximally to its full extent so that the enlarged region 11 seats within the distal end 52 of the intermediate portion 50 against the shoulder 53, so that an effective fluid-tight seal is formed between the outside of the catheter and the inside of the patient connecting member 4.

In operation, the coupling 40 of the patient connecting member 4 is secured to the tracheal tube coupling 60 and its side ports 45 and 46 are connected to a ventilator. The vacuum connecting member 3 is connected to the suction source 5 but, as long as the manual valve 32 remains unactuated, no suction is applied to the catheter 1. While ventilation takes place and the aspirating catheter 1 remains in its proximal position, no ventilation gas can flow through the intermediate section 50 of the patient connecting member 4. This prevents any significant inflation of the sleeve 2 while allowing it to remain sealed and prevent contamination escaping onto the clinician.

When aspiration of undesirable fluid from the trachea or bronchi is required, the user manipulates the catheter 1 through the sleeve 2 and pushes it forwardly so that the distal, patient end 11 of the catheter is advanced through the patient connecting member 4 and into the tracheal tube 61. When the catheter 1 has been inserted to the desired depth, the user depresses the valve 32 so that the catheter is connected to the suction source 5 and fluid in the vicinity of the tip of the catheter is sucked into the catheter and removed. During aspiration, ventilation of the patient occurs normally and some ventilation gas may seep into the envelope 2 between the outside of the catheter 1 and the inside of the intermediate portion 50. This is because the distal region 11 is no longer seated in the intermediate portion 50 and because the nature of the sponge disc 48 is such as to allow a limited gas flow both through its bulk and around the outside of the catheter 1. This small seepage of air is not a significant problem because it only occurs for a relatively short time, during aspiration. Also, the sleeve 2 is in a compressed state while aspiration occurs. It will be appreciated that other forms of sliding seal could be used instead of the sponge 48, which provide more effective seals, if required.

When aspiration is complete, the catheter 1 is pulled proximally back into the sleeve 2 to its full extent and the distal region 11 of the catheter reestablishes a seal. The assembly remains attached to the tracheal tube connector 60 so that it can be reused when necessary.

Various alternative shapes of enlargement could be provided on the outside of the aspirating catheter 1 to provide a seal with the patient connecting member 4.

Figure 3:
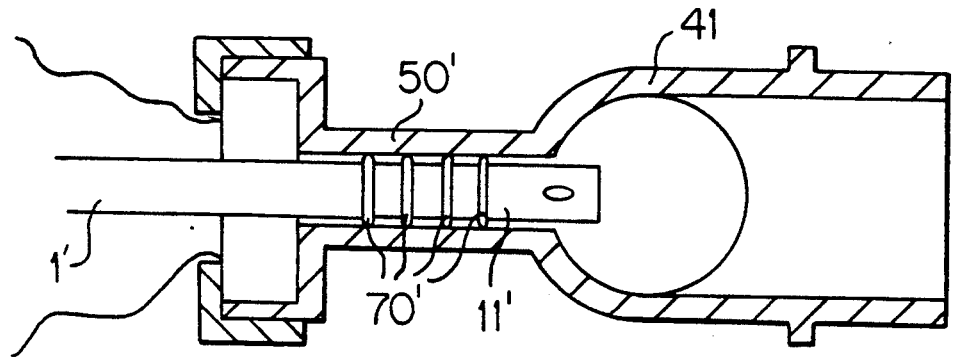
FIG. 3 is an enlarged sectional side elevation of the patient connecting member of an alternative assembly.

For example, FIG. 3 shows an arrangement in which the catheter 1' has a series of four projecting annular flanges or ribs 70' spaced from one another along the distal region 11' of the catheter and which are a close sliding within an intermediate portion 50' of cylindrical shape. Engagement of the ribs 70' with the inside of the patient connecting member 4' forms a labyrinth seal.

Figure 4:
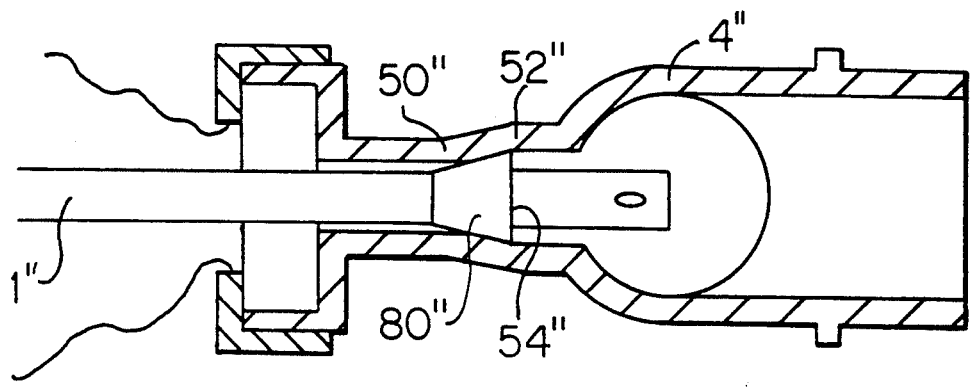
FIG. 4 is an enlarged sectional side elevation of the patient connecting member of a further alternative assembly.

In the arrangement of FIG. 4, the catheter 1" has a frusto-conical member 80" attached to its exterior close to its distal end, the frusto-conical member tapering to an enlarged diameter distally. The patient connecting member 4", in this embodiment, has a frusto-conical region 50" against which the catheter 1" seats when pulled proximally. The peripheral edge 54" of the frusto-conical region 50" forms a sliding seal with the distal end 52" of the intermediate tubular portion 50' of the patient connecting member 4".

In the arrangements of FIGS. 3 and 4, the interior of the catheter has a bore of constant diameter along its entire length.

What we claim is:

1. A suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a first fluid seal in the form of a sliding seal with the outside of the aspirating catheter; a protective sleeve surrounding at least the majority of the length of the catheter where it extends between the vacuum connecting member and the patient connecting member, the protective sleeve being adapted to permit the catheter to be extended from the protective sleeve into the patient and to be withdrawn from the patient; and the aspirating catheter having a radially enlarged portion close to its distal end which forms a second fluid seal in addition to said first sliding seal with the inside of the patient connecting member when the aspirating catheter is pulled proximally to its full extent into the protective sleeve so that gas is effectively prevented from flowing into the protective sleeve via the patient connecting member.

2. A suction catheter assembly according to claim 1, wherein the patient connecting member has a tubular portion with a distal region and a proximal region, wherein the distal region has an internal diameter that is the same as the external diameter of the enlarged portion of the catheter, and the proximal region has an internal diameter slightly greater than the external diameter of the aspirating catheter proximally of the enlarged portion such that the enlarged portion of the catheter forms a fluid seal with the distal region of the tubular portion of the patient connecting member.

3. A suction catheter assembly according to claim 2, wherein the tubular portion of the patient connecting member has a shoulder between the proximal and distal regions, wherein the aspirating catheter has a shoulder between the enlarged portion of the catheter and that part of the catheter proximally of the enlarged portion, and wherein the shoulders of the patient connecting member and the aspirating catheter are of cooperating shape and engage one another when the catheter is pulled proximally to its full extent into the protective sleeve.

4. A suction catheter assembly according to claim 1, wherein the radially enlarged portion is of constant external diameter and extends along the catheter for a distance exceeding the external diameter.

5. A suction catheter assembly according to claim 1, wherein the aspirating catheter has a plurality of radially enlarged portions in the form of a plurality of projecting flanges spaced from one another along the distal end of the catheter.

6. A suction catheter assembly according to claim 1, wherein the radially enlarged portion is of frusto-conical shape, and wherein the patient connecting member has a frusto-conical region in which the enlarged portion of the catheter seals when the catheter is pulled proximally to its full extent.

7. A suction catheter assembly according to claim 1, wherein said first sliding seal is only a limited seal that allows a limited gas flow into the protective sleeve when the aspirating catheter is in a position in which the radially enlarged portion is located in a distal position where it does not form said second fluid seal with the patient connecting member.

8. A suction catheter assembly according to claim 7, wherein the first sliding seal is provided by a member of a sponge material.

9. A suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a first fluid seal in the form of a sliding seal which seals with the outside of the aspirating catheter; the first sliding seal allowing a limited fluid flow through it; a protective sleeve surrounding at least the majority of the length of the catheter where it extends between the vacuum connecting member and the patient connecting member, the protective sleeve being adapted to permit the catheter to be extended from the protective sleeve into the patient and to be withdrawn from the patient; and wherein the distal end of the aspirating catheter includes at least one annular surface formation that engages at least one cooperating surface of the patient connecting member thereby forming a second seal only when the aspirating catheter is withdrawn from patient into a proximal position thereby preventing fluid flow into the protective sleeve via the patient connecting member.

10. A method of suctioning a patient comprising the steps of: providing a suction catheter assembly comprising an aspirating catheter having a proximal end and a distal end the distal end of the aspirating catheter having a radially enlarged sealing portion, a vacuum connecting member located in the vicinity of the proximal end of the catheter, a patient connecting member mounted to surround the aspirating catheter in the vicinity of the distal end of the aspirating catheter, the patient connecting member having a sliding seal with the outside of the aspirating catheter, and a protective sleeve surrounding at least the majority of the length of the catheter where it extends between the vacuum connecting member and the patient connecting member; connecting the patient connecting member to a tracheal tube; connecting the vacuum connecting member to a vacuum source; advancing the aspirating catheter distally by manipulation through the protective sleeve into the tracheal tube to effect suctioning, and subsequently pulling the aspirating catheter proximally to its full extent such that said enlarged sealing portion forms a seal with the inside of the patient connecting member additional to said sliding seal, only in this position of the catheter. R

* * * * *